US007721729B2

(12) United States Patent
Von Hollen et al.

(10) Patent No.: US 7,721,729 B2
(45) Date of Patent: May 25, 2010

(54) NEBULIZING DRUG DELIVERY DEVICE FOR VENTILATOR

(75) Inventors: Dirk Von Hollen, Clark, NJ (US); Eric A. Lieberman, Scotch Plains, NJ (US)

(73) Assignee: RIC Investments, LLC, Wilmington, DE (US)

(*) Notice: Subject to any disclaimer, the term of this patent is extended or adjusted under 35 U.S.C. 154(b) by 1118 days.

(21) Appl. No.: 11/367,856

(22) Filed: Mar. 3, 2006

(65) Prior Publication Data

US 2006/0201500 A1 Sep. 14, 2006

Related U.S. Application Data

(60) Provisional application No. 60/659,782, filed on Mar. 9, 2005.

(51) Int. Cl.
*A61M 11/00* (2006.01)

(52) U.S. Cl. ............................ 128/200.14; 128/202.27; 128/203.12

(58) Field of Classification Search ............ 128/200.21, 128/200.16, 202.27, 205.24, 203.12, 203.15, 128/200.14; 239/338
See application file for complete search history.

(56) References Cited

U.S. PATENT DOCUMENTS 3,387,607 A 6/1968 Gauthier et al.
3,490,697 A 1/1970 Best, Jr.
3,918,641 A 11/1975 Lehmann et al.
4,007,238 A * 2/1977 Glenn ....................... 261/78.2
4,094,317 A * 6/1978 Wasnich ................ 128/200.16
4,200,093 A 4/1980 Camp
4,792,097 A * 12/1988 Kremer et al. .............. 239/338
4,820,453 A 4/1989 Huang
4,951,661 A 8/1990 Sladek
4,976,259 A 12/1990 Higson et al.
5,062,419 A 11/1991 Rider
5,209,225 A * 5/1993 Glenn ................... 128/200.14
5,241,954 A * 9/1993 Glenn ................... 128/200.18
5,277,175 A 1/1994 Riggs et al.
5,485,827 A 1/1996 Zapol et al.

(Continued)

FOREIGN PATENT DOCUMENTS

RU 2070062 - RU 12/1996

(Continued)

*Primary Examiner*—Justine R Yu
*Assistant Examiner*—Christopher Blizzard
(74) *Attorney, Agent, or Firm*—Timothy A. Nathan (57) ABSTRACT

The present invention provides a drug delivery device having a housing that includes a ventilator interface module and a base module removeably coupled to the ventilator interface module. An aerosol generator is disposed in the base module to nebulize a drug solution provided in the housing. The ventilator interface module has an outlet port through which nebulized particles of the drug solution can be communicated to a user, and an inlet port through which the housing receives intake gas. The housing has a flow path defined therein that directs intake gas from the inlet port to the outlet port such that the nebulized drug solution particles formed in the housing are motivated toward the outlet port when the base module is coupled to the ventilator interface module. A seal arrangement substantially seals the inlet port and outlet port from ambient atmosphere when the base module is uncoupled from the ventilator interface module, such that intake gas can be communicated from the inlet port to the outlet port.

8 Claims, 10 Drawing Sheets

U.S. PATENT DOCUMENTS

| | | | |
|---|---|---|---|
| 5,687,715 | A | 11/1997 | Landis et al. |
| 5,707,352 | A | 1/1998 | Sekins et al. |
| 5,724,965 | A | 3/1998 | Handke et al. |
| 5,865,171 | A | 2/1999 | Cinquin |
| 5,908,158 | A | 6/1999 | Cheiman |
| 6,152,383 | A | 11/2000 | Chen |
| 6,202,642 | B1 | 3/2001 | McKinnon et al. |
| 6,234,167 | B1 | 5/2001 | Cox et al. |
| 6,241,162 | B1 | 6/2001 | Takahashi et al. |
| 6,283,118 | B1 | 9/2001 | Lu |
| 6,328,030 | B1 | 12/2001 | Kidwell et al. |
| 6,357,671 | B1 | 3/2002 | Cewers |
| 6,402,046 | B1 | 6/2002 | Loser |
| 6,443,146 | B1 | 9/2002 | Voges |
| 6,478,754 | B1 | 11/2002 | Babaev |
| 6,516,802 | B2 | 2/2003 | Hansen et al. |
| 6,530,570 | B2 | 3/2003 | Ku |
| 6,550,476 | B1 | 4/2003 | Ryder |
| 6,640,804 | B2 | 11/2003 | Irvi et al. |
| 6,725,858 | B2 * | 4/2004 | Loescher ............... 128/200.14 |
| 6,727,446 | B1 | 4/2004 | Mayo et al. |
| 6,854,465 | B2 | 2/2005 | Bordewick et al. |
| 7,080,643 | B2 * | 7/2006 | Grychowski et al. ... 128/200.21 |
| 7,089,941 | B2 | 8/2006 | Bordewick et al. |
| 2002/0011248 | A1 | 1/2002 | Hansen et al. |
| 2002/0082666 | A1 | 6/2002 | Babaev |
| 2003/0205229 | A1 | 11/2003 | Crockford et al. |
| 2004/0025882 | A1 | 2/2004 | Madaus et al. |
| 2005/0042170 | A1 | 2/2005 | Jiang et al. |
| 2006/0243274 | A1 | 11/2006 | Lieberman et al. |

FOREIGN PATENT DOCUMENTS

| | | |
|---|---|---|
| RU | 2076746 - RU | 4/1997 |
| WO | WO95/26236 A1 | 10/1995 |
| WO | WO 2004/017848 | 3/2004 |

\* cited by examiner

NEBULIZING DRUG DELIVERY DEVICE FOR VENTILATOR

CROSS-REFERENCE TO RELATED APPLICATIONS

This application claims priority under 35 U.S.C. §119(e) from provisional U.S. patent application Ser. No. 60/659,782 filed Mar. 9, 2005 the contents of which are incorporated herein by reference.

BACKGROUND OF THE INVENTION

1. Field of the Invention

The present invention relates to drug delivery systems, and, in particular, to nebulizing drug delivery devices used in ventilator systems.

2. Description of the Related Art

Conventional ventilator drug nebulizers are known in the medical device industry for use in delivering nebulized particles of a drug solution to a user. Such devices are typically installed in a ventilator circuit such that the gas within the ventilator circuit flows through the nebulizing drug delivery device on its path to the user. Typically, the drug nebulizer has a sealed housing that interfaces with the ventilator circuit, and into which a drug solution is provided. When the drug solution within the drug nebulizer housing is depleted, the housing must be opened in order to be replenished with additional drug solution. In some conventional drug nebulizers, opening the device housing to replenish the drug solution will result in the ventilator circuit being exposed to atmospheric air. Such atmospheric air, if introduced into the ventilator circuit, may be undesirable in certain instances. In other conventional drug nebulizers, while atmospheric air may not enter the ventilator circuit to a significant extent, gas from the ventilator circuit may leak to atmosphere when the nebulizer housing is opened for replenishing drug solution. Again, in some instances such leaking of the ventilator gas flow to atmosphere may be undesirable.

SUMMARY OF THE INVENTION

In accordance with the broad teachings of the invention, one aspect of the invention relates to a nebulizing device comprising a housing that includes a ventilator interface module and a base module removeably coupled to the ventilator interface module. An aerosol generator is disposed in the base module and is constructed and arranged to nebulize a drug solution provided in the housing. The ventilator interface module has an outlet port through which nebulized particles of the drug solution can be communicated to a user, and has an inlet port through which the housing receives intake gas. The housing has a flow path defined therein that directs intake gas from the inlet port to the outlet port such that the nebulized drug solution particles formed in the housing are motivated toward the outlet port when the base module is coupled to the ventilator interface module. A seal arrangement substantially seals the inlet port and outlet port from ambient atmosphere when the base module is uncoupled from the ventilator interface module, such that intake gas can be communicated from the inlet port to the outlet port.

In one embodiment, the device may comprise a separator structure provided in the ventilator interface module that substantially separates larger drug solution droplets from nebulized drug solution particles formed by the aerosol generator.

In another embodiment, the flow path directs intake gas directly from the inlet port to the outlet port so as to bypass a separator structure when the base module is uncoupled from the ventilator interface module.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

A specific embodiment of the invention is now described with reference to the accompanying drawings, wherein.

DETAILED DESCRIPTION OF THE PRESENTLY PREFERRED EMBODIMENTS OF THE INVENTION

Figure 1:
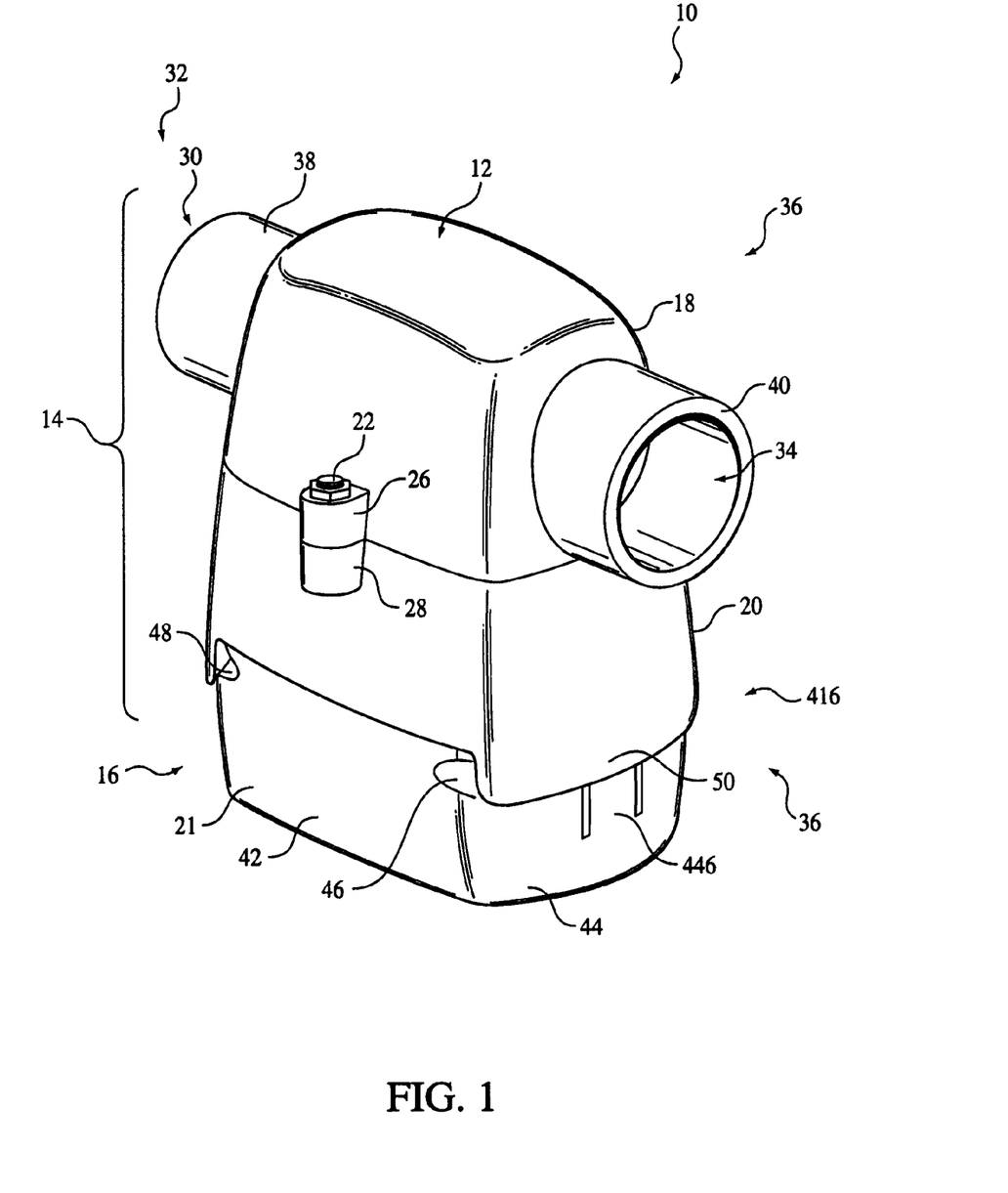
FIG. 1 illustrates a perspective view of the nebulizing device in accordance with an embodiment of the invention.
Figure 2A:
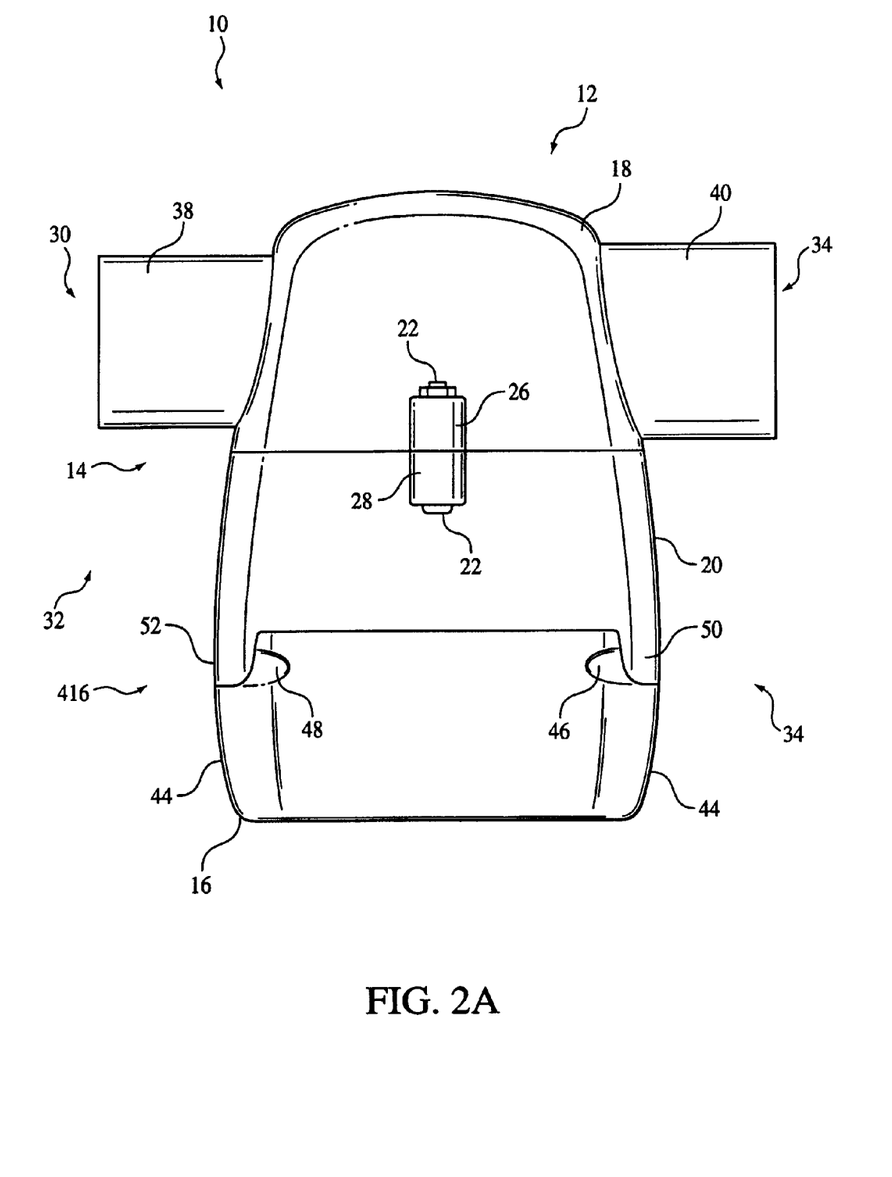
FIGS. 2A-2C illustrate elevational views of a first side, an inlet end, and an outlet end of the nebulizing device in accordance with an embodiment of the invention.
Figure 2B:
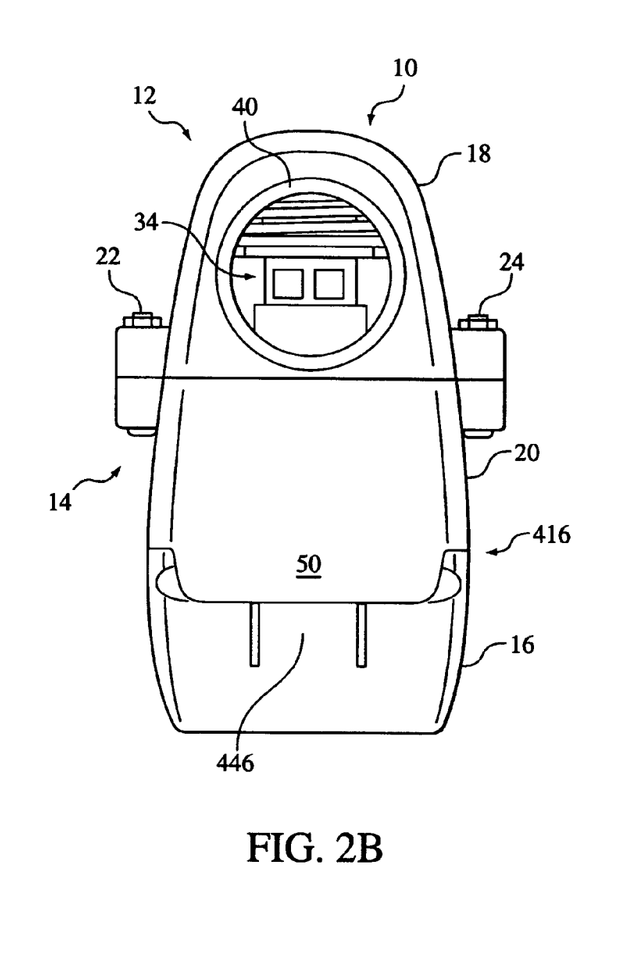
Figure 2C:
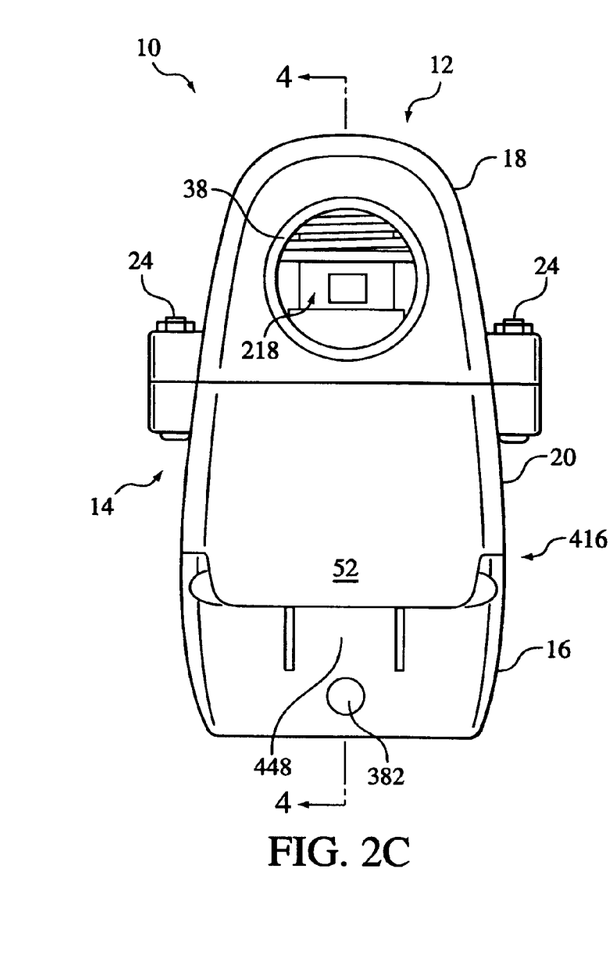

FIGS. 1 and 2A-2C are exemplary illustrations of an in-line nebulizing device 10 in accordance with the present invention. Device 10 includes a housing 12 comprising a ventilator interface module 14 and a base module 16. Ventilator interface module 14 includes an upper ventilator interface housing 18 and a lower ventilator interface housing 20. The base module 16 has an outer housing 21. As is illustrated in FIGS. 2B and 2C, upper ventilator interface housing 18 and lower ventilator interface housing 20 are coupled together via a first fastener 22 on a first side of housing 12 and a second fastener 24 on a second side of housing 12. The first fastener 22 extends through openings formed through projections 26, 28 disposed at a lower end of the upper ventilator interface housing 18 and upper end of lower ventilator interface housing 20, respectively. In other embodiments, upper ventilator interface housing 18 and lower ventilator interface housing 20 may be securely coupled via one or more of a weld, an adhesive bond, a snap-fit, or other mechanisms for securely coupling components.

Referring to FIGS. 1 and 2A, ventilator interface module 14 includes a gas inlet port 30 at inlet portion 32 of device 10 and a gas outlet port 34 at outlet portion 36 of device 10. Inlet port 30 is formed by a hollow tubular inlet port wall 38 that extends outwardly from ventilator interface module 14. Outlet port 34 is formed by a hollow tubular outlet port wall 40 that extends outwardly from ventilator interface module 14 in an opposite direction from the inlet port 30. As is illustrated in FIGS. 2B and 2C, tubular inlet port wall 38 and tubular outlet port wall 40 may be cylindrical in shape, but other tubular conduit configurations may alternately be employed.

Figure 3:
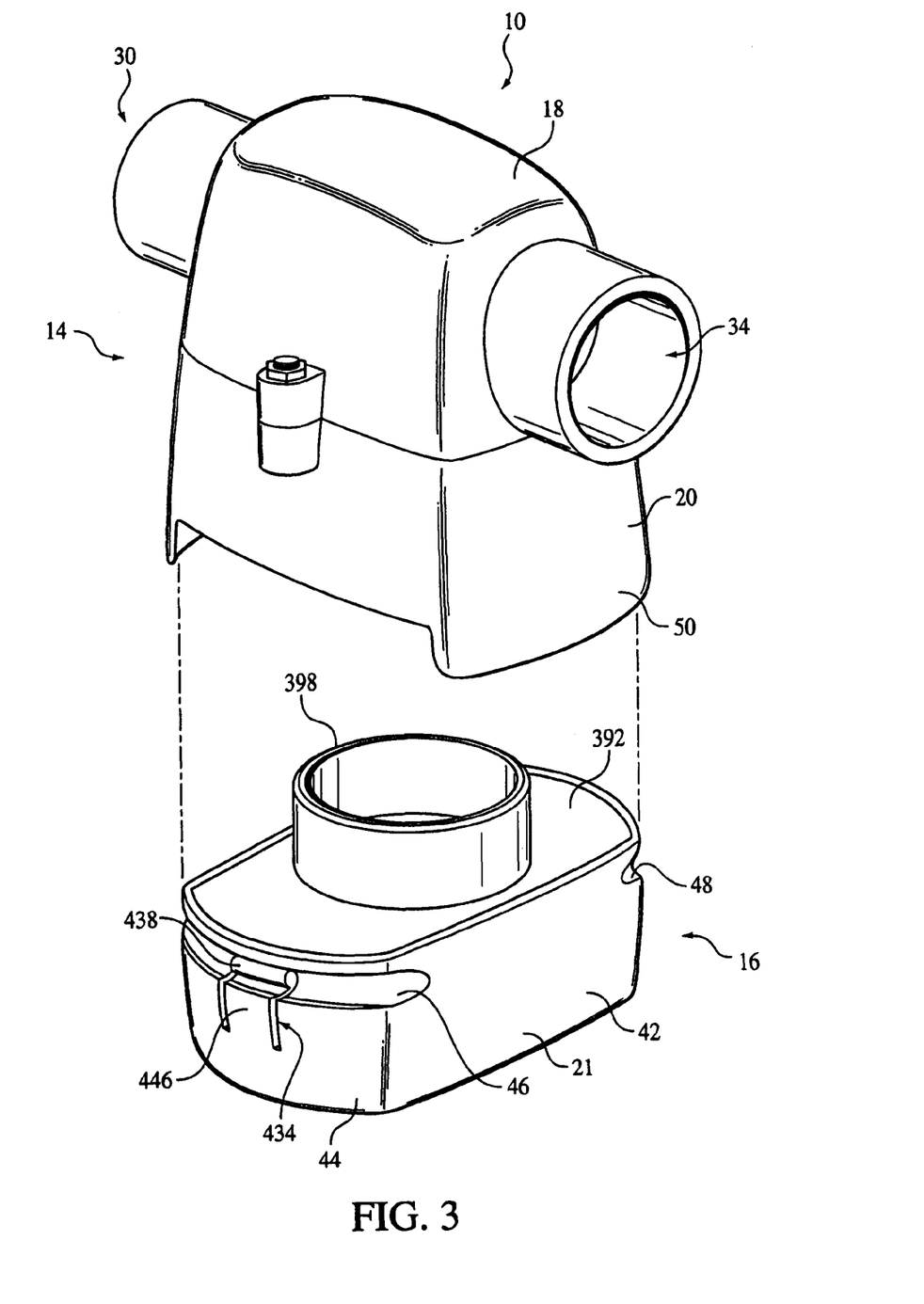
FIG. 3 is an exploded perspective view that illustrates a ventilator interface module and a base module of the nebulizing device arranged in an uncouple position, according to one embodiment of the invention.

As illustrated in FIG. 3, the ventilator interface module 14 and base module 16 can be manually coupled and decoupled from one another. More particularly, the outer housing 21 has opposite, generally flat and parallel upstanding wall portions 42. The generally parallel wall portions are connected at opposite ends thereof by outwardly projecting curved wall portions 44. The upper ends of the curved wall portions 44 have respective arcuate channels 46 and 48 formed therein as shown in FIG. 3 and the cross-sectional view of FIG. 4. As can also be appreciated from FIG. 4, the lower portion of lower ventilator interface housing 20 has projecting barb regions 50 and 52, which are configured to be received in the channels 46 and 48, respectively, for coupling and decoupling the ventilator interface module 14 to the base module 16 as will be described in greater detail below.

In general, it should be appreciated that the ventilator interface module 14 is adapted to be connected with a ventilator line. Specifically, the inlet port 30 is adapted to be connected with the output tubing of a ventilator system, and the outlet port 34 is adapted to be connected with tubing that will communicate aerosolized drug particles to a user. The ventilator interface module 14 contains a separator structure 56 disposed within the flow path between the inlet port 30 and outlet port 34. The separator structure 56 provides a circuitous flow path within the ventilator interface module that causes the larger droplets of drug solution to remain within the housing 12, while permitting the smaller nebulized particles to exit through the outlet port 34. As will be described in more detail later, ventilator interface module 14 advantageously provides an internal structural arrangement that will generate a direct flow path from inlet port 30 to the outlet port 34, thus bypassing the flow path region within the separator structure 56 when the base module 16 is decoupled from the ventilator interface module 14. As a result, the inlet port 30 and outlet port 34 remain sealed from atmosphere even when the base module 16 is decoupled. In addition, gas can continue to flow from the tubing connected to the inlet 30 to the tubing connected with the outlet 34 even when the base module 16 is decoupled. As will be described, in one embodiment, this is accomplished by sealing off the separator structure region of the flow path.

It will also be appreciated that, in general, the base module 16 includes a drug solution container 60 for containing the drug solution to be nebulized. A pool of drug solution 62 (e.g., see FIG. 7) can be provided into the container 60. In one embodiment, the pool of drug solution 62 is a metered dose of drug solution provided into the container 60 by the operator of device 10. The base module 16 also contains an aerosol generator 66 that can be operated to generate nebulized particles of drug solution from the drug solution 62 provided in the container 60, as will be described in greater detail later. It should be appreciated that many different types of aerosol generators are known and may be used in accordance with the principle of the present invention. In one embodiment, the aerosol generator 66 comprises a concave shaped piezoelectric transducer that communicates acoustic waves to the drug solution 62 through an acoustic wave transmitting fluid 70 (see FIG. 7). The fluid 70 is separated from the drug solution 62 by a barrier member 412, as will be described later. Other structural and functional characteristics of aerosol generators that may be used are described in PCT application no. PCT/AU2003/001079 (International Publication No. 2004/017848) which is hereby incorporated by reference. In addition, various other aerosol generators could be utilized without departing from the unique aspects of the present invention. The aerosol generator may include any contemporary aerosol generator such as nebulizers that utilize a planar transducer, a vibrating mesh, vibrating plate, electro spray to generate an aerosol.

FIG. 5. is a cross-sectional view of an embodiment device 10, taken along cross-section line 4-4 in FIG. 2C. As shown, lower ventilator interface housing 20 includes a lower ventilator interface outer member 310, a guide channel member 312, and a channel support 314. Lower ventilator interface outer member 310 provides an outer surface of lower ventilator interface housing 20. Guide channel member 312 forms a guide channel 316 in a longitudinal direction within a central region of ventilator interface module 14. Guide channel member 312, includes a channel sealing surface 318 at an upper end of guide channel 316. Channel support 314 is disposed between guide channel member 312 and lower ventilator interface outer member 310, and provides a structural connection between guide channel member 312 and lower ventilator interface outer member 310. Channel support 314 includes an upper ventilator interface housing seating surface 320.

Upper ventilator interface housing 18 has an opening defined by an interface housing rim 324. Upper ventilator interface housing opening defined by rim 324 is adapted to receive the separator structure 56 and other structural portions of the lower ventilator housing 20 when the upper and lower portions 18, 20 of the ventilator housing are secured together. In addition, when upper ventilator interface housing 18 and lower ventilator interface housing 20 are coupled (for example, by first fastener 22 and second fastener 24) an upper portion of guide channel member 312 is received into housing 18 via the opening defined by rim 324, and the rim 324 sits in contact with the ventilatory interface housing 320 provided on the lower ventilator housing portion 20.

The upper wall 322 of the upper ventilator interface housing 18 and the upper exterior surfaces 361 of the separator structure 56 generally define a fluid bypass passage 362. The bypass passage 362 provides for fluid communication directly from the inlet port 30 to the outlet port 34, bypassing the internal portions of the separator structure 56.

Upper wall 322 of the ventilator interface housing 18 includes a spring seating structure 328. Spring seating member 328 is adapted to retain a spring 330 at a first end of spring 330. The spring 330 extends through the fluid bypass passage 362 and has a second end thereof engaging an upper planar region 340 of the separator structure 56.

As shown, separator structure 56 includes a separator inlet region 334, a first aerosol region 336, a second aerosol region 338, and a planar separator member 340. Separator inlet region 334 is defined by an outer separator wall 342, a first inner separator wall 344, planar separator member 340, and a separator inlet region opening 346. A separator inlet 348 permits fluid to be introduced into separator inlet region 334, which in turn allow fluid to be transmitted to the first aerosol region 336 through an opening or inlet 352 into the first aerosol region 336. Separator structure 56 is rotationally oriented within guide channel 316 such that separator inlet 348 is aligned with inlet port 30, as is shown in FIG. 2C.

First aerosol region 336 is generally defined by aerosol region ceiling 350, first inner separator wall 344, inlet 352, second inner separator wall 354, and an aerosol region passage 356 formed by second inner separator wall 354 and aerosol region ceiling 350.

Second aerosol region 338 is defined by aerosol region ceiling 350, aerosol region passage 356, a drug return 358, and outer separator wall 342. Drug return 358 is disposed in a lower portion of second aerosol region 338, and includes a drug return opening 359. A separator outlet 360 is formed in outer separator wall 342 that enables communication between second aerosol region 338 and outlet port 34. Separator outlet 360 is formed in outer separator wall 342 such that when separator inlet 348 is aligned with inlet port 30, separator outlet 360 is aligned with outlet port 34, as is shown in FIG. 2B.

Planar separator member 340 extends outward from separator structure 334 to form a protruding separator rim 362. Protruding separator rim 362 provides a separator sealing surface 364 that faces channel sealing surface 318.

Ventilator interface module 14 includes a guide tube 366. A first end of guide tube 366 extends into first aerosol region 336 and a second end of guide tube 366 extends out of aerosol region 336 into a drug solution container 60 associated with base module 16. Guide tube 366 is held in structural connectivity with separator structure 56 by a guide tube collar 370. Guide tube collar 370 is connected to separator structure 56 adjacent aerosol region inlet 352 by collar struts 372. Inlet openings 352 to provide communication between first aerosol region 336 and drug solution container 60.

According to various embodiments of the invention, base module 16 includes outer housing 21, an aerosol generator housing 376, a drug pool housing 378, and control electronics 380. Outer housing 21 forms a cavity 381 in which aerosol generator housing 376, a portion of drug pool housing 378, and control electronics 380 reside. A power connection opening 382 is provided in outer housing 21 to receive a power connector from an external power source. In other embodiments, device 10 may be powered by an internal power source, such as a battery, a fuel cell, or other internal power sources.

In one embodiment, aerosol generator housing 376 includes aerosol generator seating portion 384, and a rim portion 386. Drug pool housing 378 includes drug solution container 60, a barrier opening 388, a lower skirt portion 390, and a drug pool housing support 392.

An aerosol generator 66 is mounted within aerosol generator housing 376 at aerosol generator seating portion 384. As noted above, in one embodiment, and as illustrated, aerosol generator 66 comprises an acoustic wave aerosol generator that generates acoustic waves within device 10. In the embodiment illustrated in FIG. 5, and as stated above, the aerosol generator 66 comprises a concave piezoelectric transducer with a silver electrode. The piezoelectric transducer generates acoustic waves at a generator frequency, such as, in a non-limiting example, 2.5 MHz. The acoustic waves are focused by the concave configuration of the piezoelectric transducer at a focal point that is at a focal length from aerosol generator 66. Device 10 is arranged such that the focal point falls within drug solution container 60.

Aerosol generator housing 376 and drug pool housing 378 may be joined such that rim portion 386 of aerosol generator housing 376 and lower skirt portion 390 of drug pool housing 378 define a transmitting fluid chamber 396, positioned beneath drug solution container 60. Rim portion 386 and lower skirt portion 390 may be securely joined via one or more of a weld, an adhesive bond, a fastener, a snap-fit, or other mechanisms for securely joining components.

In some embodiments, drug solution container 60, disposed within drug pool housing 378, is formed by a chamber wall 398 and a chamber floor 410. Chamber floor 410 slopes in a downward direction from chamber wall 398 to barrier opening 388, formed in chamber floor 410. Barrier opening 388 provides a pathway between transmitting fluid chamber 396 and drug solution container 60 through which acoustic waves may be communicated.

Although acoustic waves may be transmitted through barrier opening, a barrier 412 is provided at barrier opening 388 to prevent fluid communication between transmitting fluid chamber 396 and drug solution container 60. Barrier 412 is mounted across barrier opening 388 at a barrier mounting surface 414. In the embodiment shown, barrier mounting surface 414 is illustrated as being provided at an upper surface of transmitting fluid chamber 396, but alternate configurations exist. For example, barrier mounting surface 414 may be provided at chamber floor 410, or otherwise located. Barrier 412 may be composed of one or more materials that meets various design criteria. Design criteria may include, for example, a prescribed thickness, an elasticity, a durability at high temperatures, an acoustic wave transmission property, or other criteria.

Figure 4:
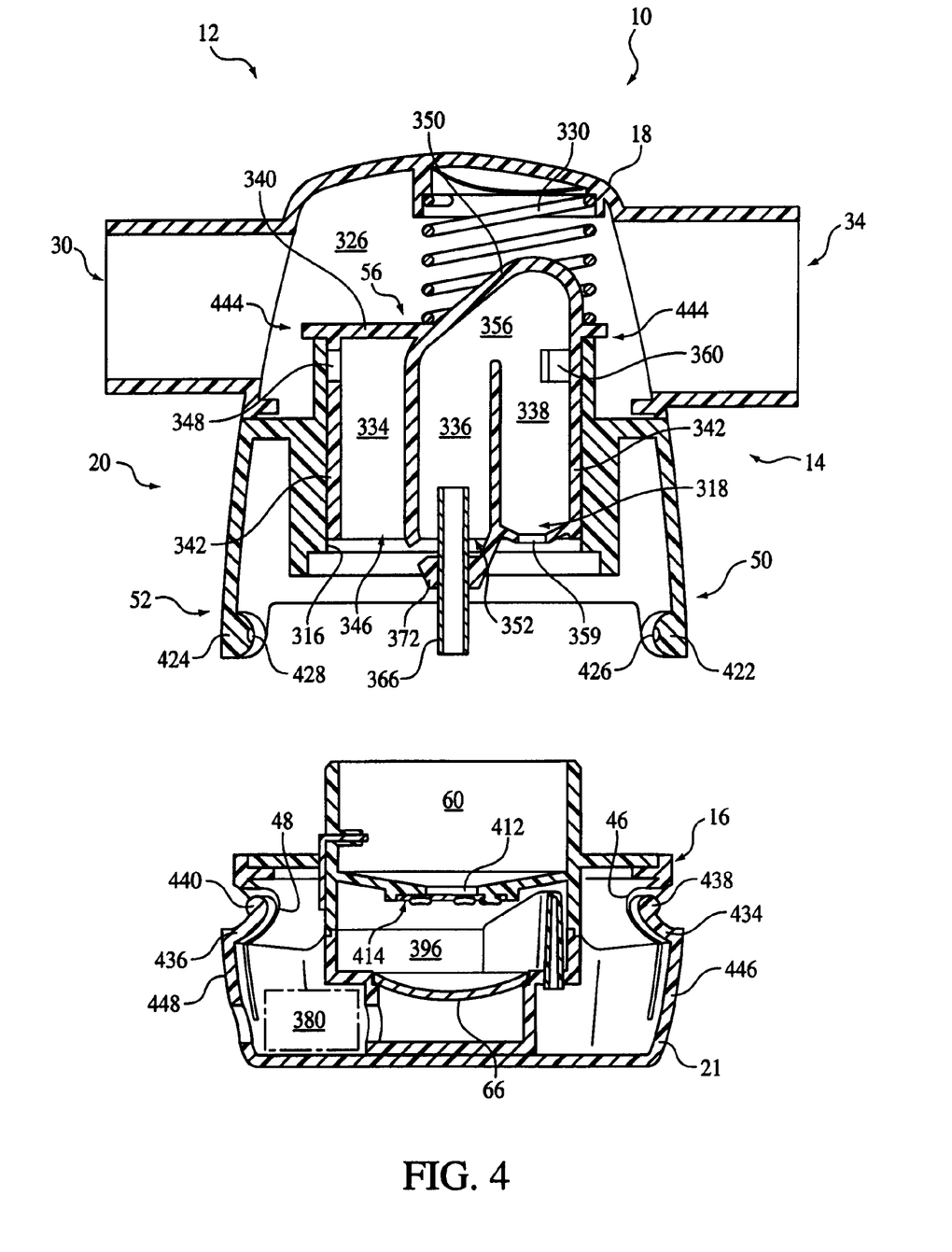
FIG. 4 illustrates an exploded sectional view of the nebulizing device of FIG. 2C, taken along section line 4-4, according to one embodiment of the invention, but showing the base module separated from the ventilator interface module.

It will be appreciated that ventilator interface module 14 and base module 16 may be formed as an integral housing, or may be securely joined to form a single unitary (or substantially unitary) housing. However, in the embodiments illustrated, ventilator interface module 14 and base module 16 are selectively coupled at a housing interface 416. As seen in FIGS. 2B, 2C, 4, and 5, at housing interface 416, ventilator interface module 14 provides a first barbed overlap 50 and a second barbed regions 52 that extend down from ventilator interface module 14. Referring to FIG. 4, first and second barbed overlaps 50 and 52 include a first overlap barb 422 and a second overlap barb 424, respectively, at inner surfaces of barbed overlaps 50 and 52. A first barb slot 426 is formed in first overlap barb 422, and a second barb slot 428 is formed in second overlap barb 424. Barb slots 426 and 428 are formed in overlap barbs 422 and 424 at central regions of inlet end 32 and outlet end 34 of device 10.

At housing interface 416, base module 16 provides a first interface channel 46 and a second interface channel 48. As is shown in FIG. 3, interface channels 48 and 432 run along the base module 16, the length of inlet end 32 and outlet end 34, respectively. Referring back to FIG. 4, a first biased tab 434 and a second biased tab 436 are provided by base module 16 at housing interface 416. A first tab barb 438 and a second tab barb 440 are disposed on first biased tab 434 and second biased tab, respectively. Biased tabs 434 and 436 are provided by base module 16 such that an upper portion of biased tabs 434 and 436 are arranged within interface channels 46 and 48. As is illustrated in FIG. 3, biased tabs 434 and 436 are provided by base module 16 at the central regions of inlet end 32 and outlet end 34, such that when ventilator interface module 14 and base module 16 are coupled, tab barbs 438 and 440, disposed on biased tabs 434 and 436, align with barb slots 426 and 428, as shown in FIG. 5.

Figure 5:
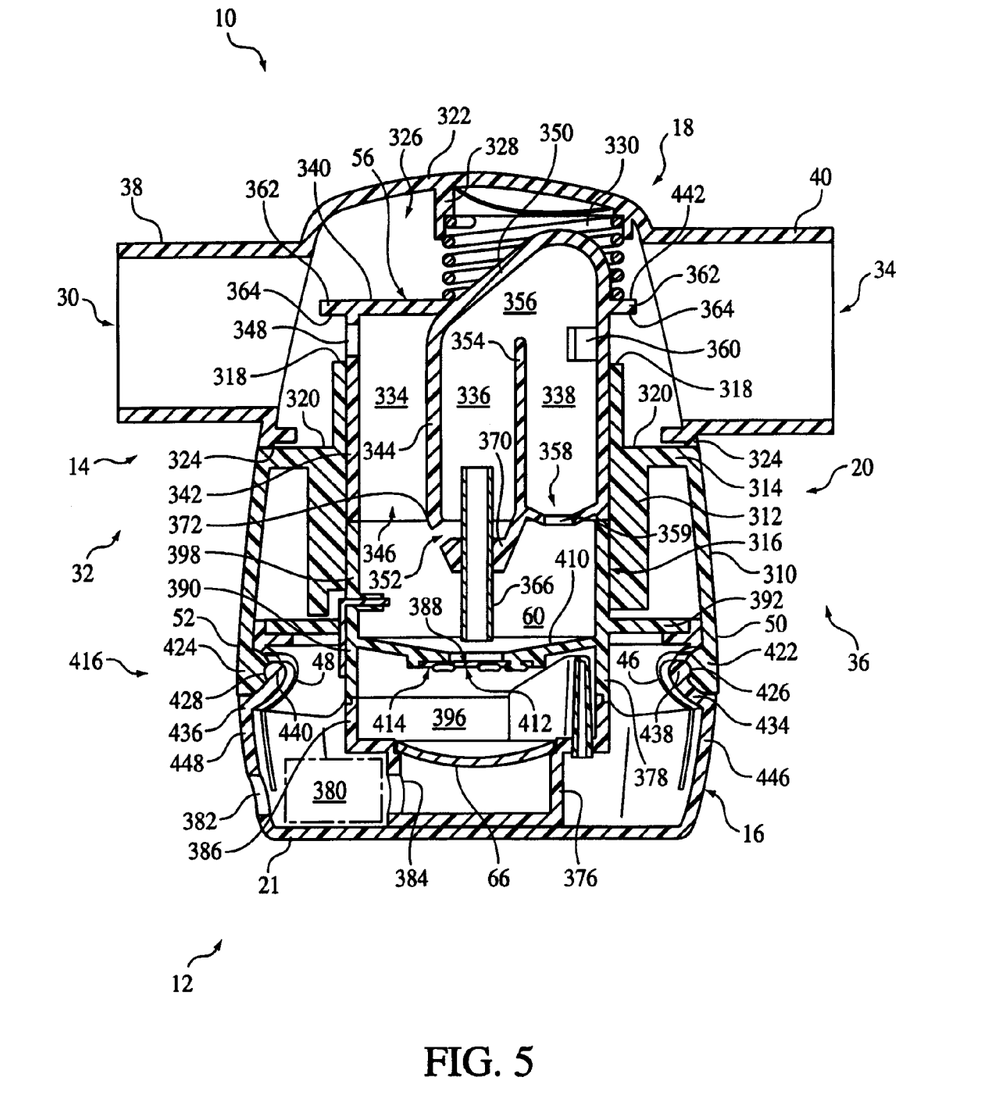
FIG. 5 illustrates a sectional view of the nebulizing device similar to FIG. 4, but showing the base module coupled to the ventilator interface module.

Still referring to FIG. 5, when ventilator interface module 14 is coupled to base module 16, drug solution container 60 of drug pool housing 378 is received into guide channel 316. When drug solution container 60 is received into guide channel 316, an upper edge of chamber wall 398 interfaces with a lower edge of outer separator wall 342. Outer separator wall 342 is maintained in contact with chamber wall 398 by virtue of a downward bias applied to separator structure 56 by spring 330 at a separator spring surface 442, provided by planar separator member 340.

Turning to FIG. 4, when ventilator interface module 14 is uncoupled from base module 16, drug solution container 60 is withdrawn from guide channel 316, which removes chamber wall 398 from contact with outer separator wall 342. In the absence of this contact, the bias applied by spring 330 forces separator structure 56 to slide downwardly within guide channel 316 until separator inlet 348 and separator outlet 360 drop below channel sealing surface 318 of guide channel 316, thus sealing inlet separation 348 and outlet 360 of the separator structure 56 from inlet 30 and outlet 34. In addition, separator sealing surface 364 engages channel sealing surface 318. The engagement between separator sealing surface 364 and channel sealing surface 318 forms a seal arrangement 444 that seals the internal passage of the separator structure from the flow bypass cavity 326. This retains sealed communication from the inlet port 30 to the outlet port 34 through the flow bypass cavity 326, without leakage to or from ambient air.

In the illustrated embodiment, spring 330 is a compressible coil spring. It should be appreciated, however, that spring 330 is merely one example of a device capable of biasing. Springs of many different types could be employed to generate the sealing action, such as leaf springs, torsion springs, or resilient biasing materials. In addition, one of ordinary skill in the art can best appreciate that various other biasing mechanisms other than springs could be used to bias separator structure 56 such as properly aligned magnets (including permanent magnets and electromagnets), or shape memory alloys, and the like.

In addition, other structures for the sealing arrangement 444 can be used. For example, in one embodiment, the sealing arrangement includes an electric or pneumatically operated actuator rather than a spring to moves the separator structure 56 downwardly to create a sealed passage from the inlet port 30 to the outlet port 34 when the base module 16 is removed. In this arrangement, various mechanism can be used to detect that the base module 16 has been decoupled from the ventilator interface module 14. For example, in one contemplated configuration, a light-pipe detector circuit would be carried by the ventilator interface module 14. The light pipe detector circuit can detect when the base module 16 has been decoupled as a result of a conduit between a signal transmitter output and a signal receiver input being disrupted. Further details of such an arrangement, and other arrangements for detecting that the base module 16 has been decoupled will be appreciated from co-pending U.S. Application Ser. No. 60/659,778, entitled NEBULIZING DRUG DELIVERY DEVICE WITH INTERLOCK AND DETECTION AND TEMPERATURE PROTECTION, and from co-pending U.S. application Ser. No. 60/659,781 entitled NEBULIZING DRUG DELIVERY DEVICE WITH BARRIER, each of which is filed on even date herewith and hereby incorporated by reference in its entirety. It is further contemplated that such a detection circuit can alternatively, or in addition, be carried by base module 16 and used to disable the aerosol generator 66 when base module 16 has been decoupled from the ventilator interface module 14, as can also be appreciated from the aforementioned co-pending U.S. Applications.

In another contemplated embodiment, the separator structure 56 can remain stationary, and the sealing arrangement 444 can take the form of one or more valves that create a sealed passage from the inlet port 30 to the outlet port 34 when the base module 16 is decoupled from the ventilator interface module. This can be accomplished by having a pair of valves (such as solenoid valves) seal separator inlet 348 and separator outlet 360 when a detector detects that the base module 16 has been decoupled. Thus, flow from inlet 30 will only travel through the bypass passage to the outlet port 34 and bypass the separator structure 56.

In yet another embodiment, it is contemplated that valves can be provided at the separator inlet region opening 346 and drug return opening 359. In this arrangement, fluid would be permitted to pass through not only the bypass passage cavity 326, but also pass through the internal regions 334, 336, 356 of the separator structure 56 before exiting the outlet port 34.

In the disclosed embodiments, when the base module 16 is uncoupled from the ventilator interface module 14, the inlet port 30 and outlet port 34 are substantially sealed from ambient atmosphere. As a result, intake gas from a ventilator can be communicated from the inlet port to the outlet port without leaking to atmosphere. In addition, atmospheric air does not leak into the flow path from the inlet port 30 to the outlet port 34, when the base module is removed.

Ventilator interface module 14 may be coupled to base module 16 by first, placing modules 14 and 16 in the position shown in FIG. 3. This includes positioning the uncoupled modules 14 and 16 so that while chamber wall 398 of base module 16 and guide channel 316 of ventilator interface module 14 are aligned along a common axis, ventilator interface module 14 and base module 16 are oriented in transverse directions. After positioning modules 14 and 16 in this manner, they are moved relative to each other along the common axis to introduce drug solution container 60 into guide channel 316.

Figure 6A:
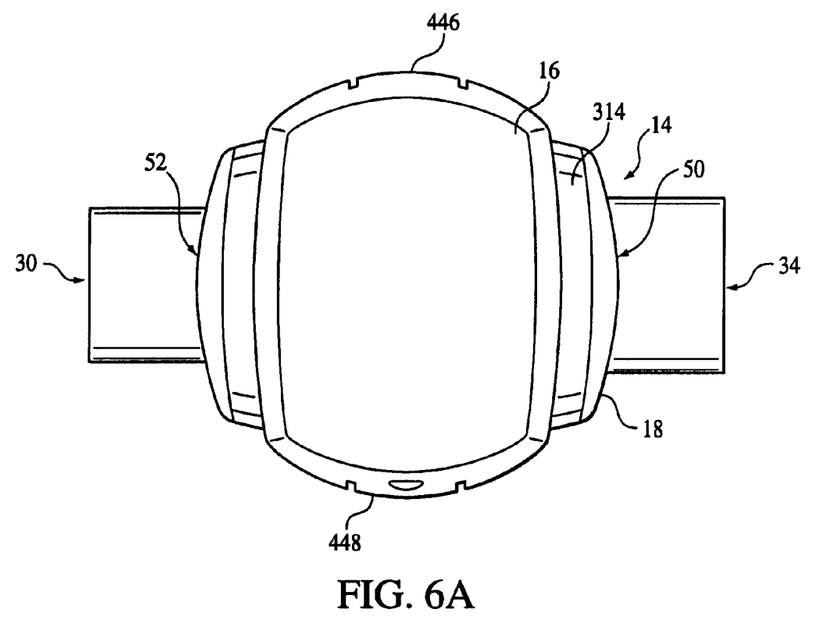
FIGS. 6A and 6B are lower plan views of the nebulizing drug delivery device, in accordance with an embodiment of the invention.
Figure 6B:
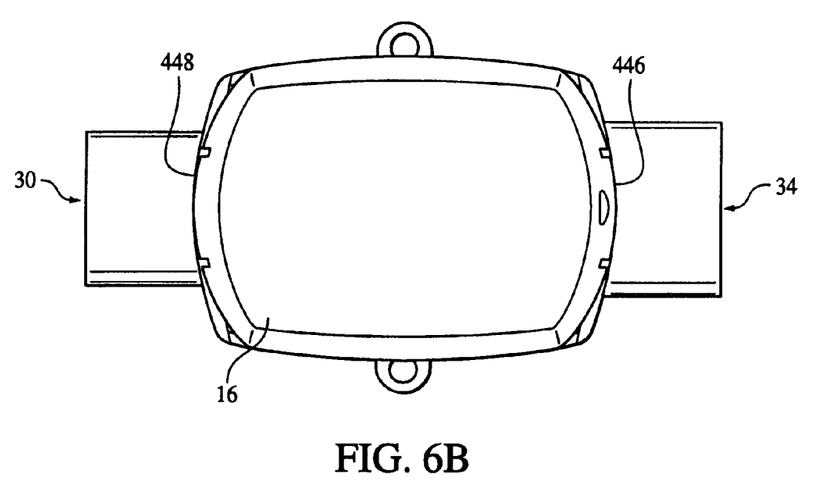

In this position, ventilator interface module 14 and base module 16 will be in contact with each other and will be in the position illustrated in the lower elevation view provided by FIG. 6A. Ventilator interface module 14 and base module 16 are then rotated with respect to each other to bring modules 14 and 16 into the position shown in the lower elevation view of FIG. 6B. Rotating ventilator interface module 14 and base module 16 will introduce first overlap barb 422 and second overlap barb 424 into first interface channel 46 and second interface channel 48, respectively. By continuing to rotate modules 14 and 16, overlap barbs 422 and 424 will be slid into interface channels 46 and 48 to couple ventilator interface module 14 to base module 16. When first overlap barb 422 and second overlap barb 424 contact, and slide along, first biased tab 434 and second biased tab 436, biased tabs 434 and 436 will be deformed inwardly into interface channels 46 and 48. As modules 14 and 16 are rotated to the alignment illustrated in FIG. 6B, first tab barb 438 and second tab barb 440 will be received into first barb slot 426 and second barb slot 428, respectively, as is illustrated in FIG. 5. Due to the outward bias of biased tabs 434 and 436 caused by deforming biased tabs 434 and 436 in an inward direction, tab barbs 438 and 440 will engage barb slots 426 and 428 to rotationally secure overlap barbs 422 and 424 within interface channels 46 and 48.

To uncouple the coupled modules 14 and 16, first biased tab 434 and second biased tab 436 can be deformed inwardly by applying an inward force at a first depressible surface 446 and a second depressible surface 448 provided on first biased tab 434 and second biased tab 436, respectively. Depressible surfaces are illustrated in FIGS. 1, 2A, 2B, 3, 4, and 5. Deforming biased tabs 434 and 436 disengages tab barbs 438 and 440 from barb slots 426 and 428, thereby enabling ventilator interface module 14 and base module 16 to be rotated to remove overlap barbs 422 and 424 from interface channels 46 and 48.

Figure 7:
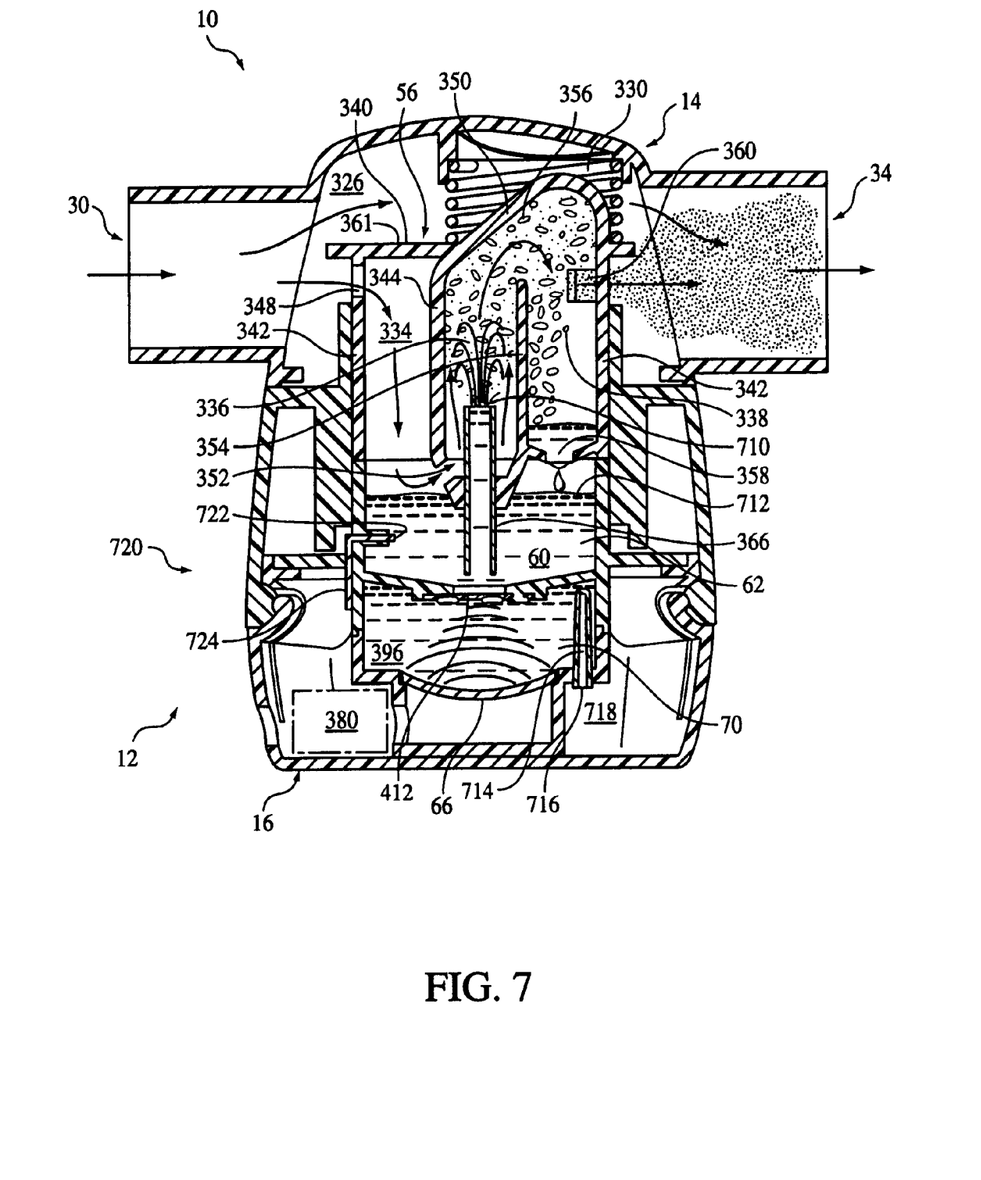
FIG. 7 is a cross-sectional view of the nebulizing device similar to FIG. 5, but illustrating the operation of the nebulizing drug delivery device, in accordance with one embodiment of the invention.

FIG. 7 is an exemplary cross-sectional view of an embodiment of device 10 during use, taken along cross-section line 3. As will be described in greater detail below, the ventilator interface module 14 generally functions to deliver nebulized drug solution particles to a user through outlet port 34. Intake gas is received into housing 12 through inlet port 30. Prior to delivery of the nebulized drug solution particles, the internal structure of ventilator interface module 14 separates larger drug solution droplets from the nebulized particles that are delivered to the user and returns such larger droplets to the drug solution 62 within container 60.

As illustrated in the cross-section of FIG. 7, the nebulized particles of the drug solution are formed in device 10 from drug solution forming the drug solution 62 held within housing 12 at drug solution container 60, which sits over aerosol generator 66. More specifically, acoustic waves are transmitted from aerosol generator 66 to the drug solution 62 via an acoustic wave transmitting fluid 70 held within transmitting fluid chamber 396. Acoustic waves are transmitted from the acoustic wave transmitting fluid 70 to the drug solution 62 via barrier 412.

In one embodiment, the transmitting fluid 70 may primarily be comprised of water. In some instances, a sterilant, such as alcohol, or another sterilant, may be added to the acoustic wave transmitting fluid 70.

As was set forth previously, the acoustic waves generated by aerosol generator 66 are focused at a focal point within the drug solution 62 formed in drug solution container 60. The drug solution present at the focal point of the acoustic waves will absorb the ultrasonic energy to create a fountain 710 from the drug solution 62. That is, the focused acoustic waves will generate a focused stream of the drug solution, which stream begins at a point that can also be considered the beginning of fountain 710. Towards the top of the stream or fountain 710, the energized drug solution within the drug solution 62 is nebulized to form aerosol drug solution particles. Some of the drug solution in fountain 710 may not be nebulized, but rather form larger droplets of the drug solution that will be returned to the drug solution 62.

In some embodiments of the invention, the nebulization of the drug solution at fountain 710 may be enhanced when the focal point of the acoustic waves coincides (exactly or substantially) with a surface 712 of the drug solution in drug solution container 60. In such embodiments, the level of surface 712 may be controlled with some particularity to enhance the operation of fountain 710.

According to some embodiments of the invention, and as previously mentioned, guide tube 366 may be disposed within device 10 such that a first end is positioned in first aerosol region 336, and a second end of guide tube 366 that extends into the drug solution 62 formed in drug solution container 60, over barrier 412. In such instances, fountain 710 can be formed within guide tube 366 as a result of the focal point being disposed proximate the second end of guide tube 366. Drug solution from the drug solution 62 may be propelled toward the first end of guide tube 366 by the ultrasonic energy from the acoustic waves. At the first end of guide tube 366, the energized drug solution stream exits guide tube 366. Nebulized (or aerosolized) particles of the drug solution are formed towards the upper portions of the steam or fountain 710 of drug solution. Guide tube 366 may increase the formation of the nebulized particles of the drug solution within fountain 710 by itself functioning to energize drug solution within guide tube 366 that is not be located at the focal point of the acoustic waves.

Continuing with reference to FIG. 7, the nebulized particles pass through device 10, from the drug solution 62 to outlet port 34, via separator structure 56. More particularly, the nebulized particles are received from guide tube 366 into first aerosol region 336, pass into second aerosol region 338, and are communicated to outlet port 34 through separator outlet 360. The nebulized particles are communicated between first aerosol region 336 and second aerosol region 338 via aerosol region passage 356. The various components of separator structure 56 may be arranged such that the nebulized particles may pass through to outlet port 34, while the larger droplets of the drug solution may, due to size and/or weight, contact surfaces of separator structure 56, such as first inner separator wall 344, second inner separator wall 354, aerosol region ceiling 350, or outer separator wall 342 and condense on the contacted surface. The drug solution included in the larger particles that condenses on separator structure surfaces in second aerosol region 338 will be returned to the drug solution 62 via second aerosol region 338. The drug solution included in the larger particles that condense on separator structure surfaces in first aerosol region 336 will return to the drug solution 62 through aerosol region inlet 352.

At inlet port 30, intake gas is received by device 10. A flow path may be established between inlet port 30 and outlet port 34 that, when ventilator interface module 14 is coupled to base module 16, directs at least a portion of the intake gas such that the intake gas motivates the nebulized particles from fountain 710, through separator structure 56, to outlet port 34.

Figure 8:
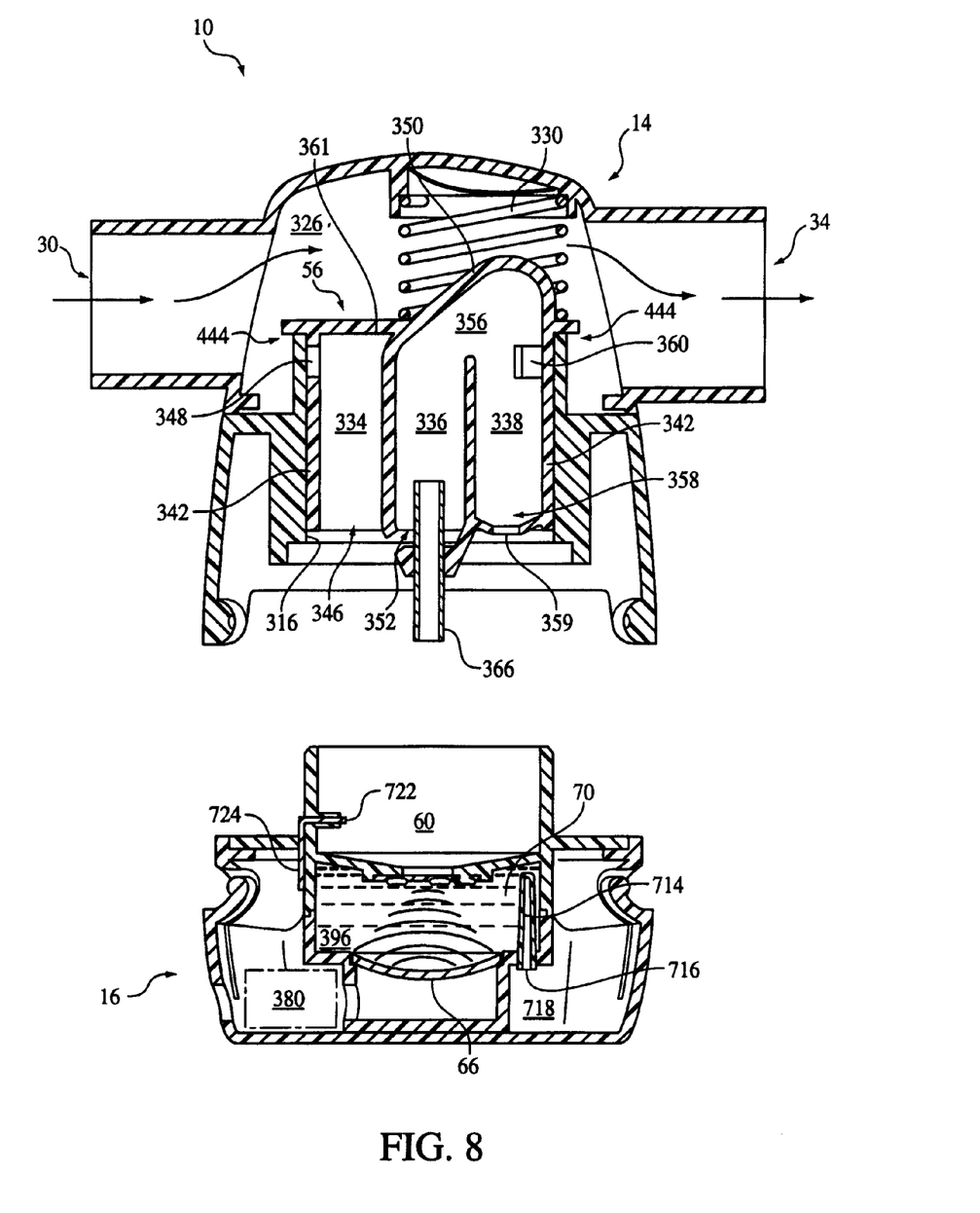
FIG. 8 is a cross-sectional view of the nebulizing device similar to FIG. 4, but illustrating the ventilator flow path after the base module has been decoupled to the ventilator interface module.

Referring again to FIG. 7, intake gas directed into separator structure 56 via separator inlet 348 flows through separator inlet region 334 and into container 60. The intake gas provided to drug solution container 60 may enter first aerosol region 336 at aerosol region inlet 352 and flow through separation inlet region 334 and first aerosol region 336 to separator outlet 360 where it will be communicated to outlet port 34. The nebulized particles formed at fountain 710 may be motivated by the flow of the intake gas along the flow path as the intake gas passes fountain 710 at aerosol region inlet 352 and proceeds toward outlet port 34. Intake gas that does not enter separator structure 56 passes directly from inlet port 30 to outlet port 34 through flow bypass cavity 326. When ventilator interface module 14 and base module 16 are uncoupled, as is illustrated in FIG. 8, sealing arrangement 444 seals the flow path from inlet port 30 to outlet port 34 by sealing flow bypass cavity 326, as has been described above. For example, the intake gas may include filtered gas provided to device 10 in a force flow along a ventilator circuit. The ventilator circuit may provide the intake gas through an operative connection at inlet port 30, and may receive the output of device 10 via an operative connection with outlet port 34. Sealing the flow path when modules 14 and 16 are uncoupled may inhibit contamination of the intake gas in the ventilator circuit.

In one embodiment of the invention, as seen most clearly in FIGS. 7, and 8, a variable volume resilient structure 714 is disposed within transmitting fluid chamber 396 and is in contact with the fluid 70 held therein. Resilient structure 714 may be reduced in volume so as to reduce the amount of space it occupies in transmitting fluid chamber 396. In one embodiment, resilient structure 714 is composed of a deformable material to accommodate expansions in the volume of the fluid 70, and thereby protect other components from damage due to changes in the volume. For instance, aerosol generator 66, barrier 412, may potentially be subject to damage in the event that ambient temperature surrounding device 10 is low enough to cause a fluid temperature of the fluid 70 to approach or reach freezing. Or, the fluid 70 may also expand as the fluid temperature rises. In the event of such expansion of the transmitting fluid 70, resilient structure 714 will reduce in volume to accommodate the increased volume of the fluid. This, for example, may prevent cracking of the transmitting fluid chamber 396.

In the figures, resilient structure 714 is illustrated in an exemplary manner as a bladder. Expansion protection bladder 714 is composed of a deformable material, such as, for instance, silicon, or other deformable materials. Bladder 714 has an opening 716 peripherally sealed to an opening in a lower surface of transmitting fluid chamber 396. Opening 716 leads into an internal space in the bladder 714 that is exposed to atmosphere. Bladder 714 may be vented to atmosphere via a passage 716 that leads to an open space 718 in housing 12. Space 718 is not sealed, and is allowed to bleed air and receive air to and from atmosphere. Because the amount of air displaced is small and only needs to be done over a long period of time, there is no need for a large vent housing 12 for this purpose, as the slow permeation of air to and from space 718 is sufficient.

It is contemplated that resilient structure 714 can be formed from different materials, or from a plurality of different members. For example, the resilient structure can be made from a sponge material. In another embodiment, resilient structure 714 may include a rigid structure that is biased into transmitting fluid chamber 396 by a spring or other resilient member. The rigid structure would form a moving seal with transmitting fluid chamber 396 and take up more or less of the chamber volume based on the fluid volume as described above.

According to one embodiment of the invention, an inner diameter of guide tube 366 may be varied to provide control over one or more aspects of the nebulization of the drug solution. For instance, by varying the inner diameter of guide tube 366, a nebulized particle size delivered to the user, a flow rate of the drug solution delivered to the user, or other aspects of the nebulization may be controlled. In a non-limiting example, guide tube 366 may include an inner diameter of between 2 mm and 3 mm, with smaller inner diameters producing smaller nebulized particles and/or a lower flow rate, and larger inner diameters producing larger nebulized particles and/or a higher flow rate.

It should be appreciated that many of the principles and features described herein can be used in an embodiment of the present invention that does not employ guide tube 366. In such a system, most of the volume of drug solution within device 10 is contained in a reservoir that feeds the drug solution to the drug solution 62 that rests on the barrier 412 as the drug solution pool becomes depleted. A valve system, such as a float valve, can be used to regulate or control distribution of the drug solution from the drug solution pool to the barrier 412.

Figure 9:
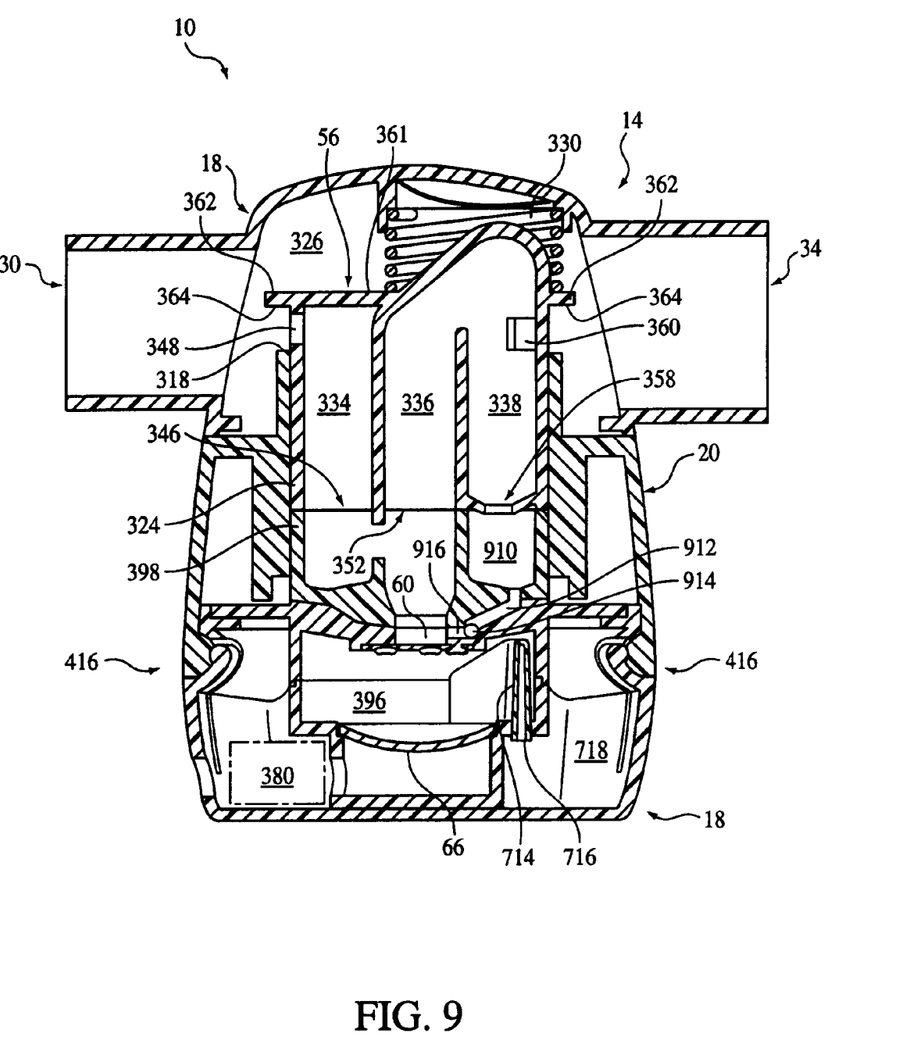
FIG. 9 illustrates a sectional view of an alternate embodiment of the nebulizing drug of the invention that does not employ a guide tube arrangement.

More particularly, in one embodiment illustrated in FIG. 9, a drug reservoir 910 may provide the drug solution to the drug solution 62 held in container 60 via a fill channel 912 to replenish the drug solution when the level of surface 712 of the drug solution drops due to nebulization, or other factors, thereby maintaining the level of surface 712 of the drug solution 62 at or proximate to the focal point of the acoustic waves generated by aerosol generator 66.

A float valve 914 may be positioned at a fill channel opening 916 in drug solution container 60 such that when the level of surface 712 rises, float 914, which is buoyant in the drug solution, rises up to block the drug solution from flowing into drug solution container 60 from fill channel 912. However, when the level of surface 712 begins to drop, float valve 914 falls away from fill channel opening 916, thereby enabling the drug solution in fill channel 912 to flow into drug solution container 60 until the level of surface 712 rises to a point where float 914 again blocks fill channel opening 916. Float valve 914 may include a ball float, or float valves of other shapes.

The large droplets of the drug solution formed at fountain 710 are separated from the nebulized particles of the drug solution formed at fountain 710 by separator structure 56. Subsequent to separation, the large droplets are returned to drug solution reservoir 910 via drug return 358.

In some embodiments of the invention, separator structure 56 may provide a drug delivery path from fountain 710 to outlet port 34 for the nebulized particles formed at fountain 710. As the nebulized particles travel along the drug delivery path, separator structure 56 provides surfaces that separate nebulized particles formed at fountain 710 from the larger droplets formed by the drug solution propelled out of the drug solution 62 prior to delivery of the nebulized particles to the user. Subsequent to separation from the nebulized particles, the larger droplets are returned to drug reservoir 910 and/or the drug solution 62.

This arrangement is disclosed more fully in co-pending U.S. patent application Ser. No. 60/659,919 entitled NEBULIZING DRUG DELIVERY DEVICE WITH INCREASED FLOW RATE, filed on even date herewith and hereby incorporated by reference in its entirety.

Returning to FIG. 7, an optional embodiment of device 10 that includes a drug solution detection system 720 is illustrated. Drug solution detection system 720 detects if the amount drug solution within the drug solution 62 falls below a threshold level based on detection of an AC electrical signal generated by aerosol generator 66. Drug solution detection system may include a probe 722, and a signal lead 724.

Probe 722 is positioned to detect the AC signal generated by aerosol generator 66 via the drug solution 62. In other words, the drug solution itself may act as a conduit for the AC signal that conducts the AC signal to probe 722. When surface 710 of the drug solution 62 falls below the threshold level, the drug solution will no longer be able to deliver the AC signal to probe 722. Although probe 722 is illustrated as being disposed within the drug solution 62, detecting the AC signal directly, in other embodiments, probe 722 may be disposed in contact with an outer surface of chamber wall 398 and may detect the AC signal capacitively through the wall.

The AC signal (or lack thereof) detected by probe 722 may be relayed to control electronics 380 via signal lead 724.

In one embodiment, when the AC signal is not detected, control electronics 380 may automatically deactivate device 10. For example, aerosol generator 66 may be deactivated. Or, control electronics 380 may activate an alert, such as, for example, a visual or audible indicia, that may warn the user that level 710 of the drug solution may have dropped below the threshold level.

The threshold level as contemplated herein can be virtually "empty". However, it may be desirable for the threshold level to be some drug solution volume above empty, to allow the user sufficient warning that the drug solution is near depletion. In addition, when the drug solution volume reaches below a certain level, its thermal mass also drops below a threshold that may make it more susceptible to temperature changes in the environment or due to components within the device itself. Such temperature changes may be undesirable, as it may alter the effectiveness of certain drug solutions. In one non-limiting example, it may be desirable in some embodiments of the present invention to provide the device 10 with a heater that heats the drug solution 62. Such a heating arrangement may be desirable to lower the viscosity of the drug solution 62, particularly when using a drug solution of a high viscosity. Such a heater may be provided in contact with the drug solution 62 itself, or surrounding drug solution container 60, as described in the aforementioned co-pending U.S. patent application Ser. No. 60/659,919 entitled NEBULIZING DRUG DELIVERY DEVICE WITH INCREASED FLOW RATE, which is incorporated by reference in its entirety. In the event that the amount of drug solution drops below a threshold level, the thermal mass of the drug solution 62 may be subject to over heating. This may prevented by disabling the aerosol generator 66 through use of control electronics 380 when the amount of drug solution drops below a threshold level as described above.

In another embodiment, it is contemplated two different drug solution levels may be detected. In such a system, a first low level is detected and provides either an audible or visual alarm to the user. This may prompt the user to refill the device 10 with drug solution, or in a disposable version, to obtain a new device 10. At this first low level point, however, the drug solution may not be sufficiently low to be disabled, and will continue to function. At a second low level point (e.g., when the drug solution 62 is of a less than desirable thermal mass) the system control electronics 380 will then disable the aerosol generator. In such a dual level detection arrangement, it is contemplated that the control electronics can sense two different current levels transmitted through the drug solution 62, as the current level decreases with the increased resistance due to drug solution depletion. In another embodiment, two different probes are provided for detecting the two different drug levels.

It should also be appreciated that many of the principles of the present invention can be employed without a level detector, or with a known, conventional level detector.

It should also be appreciated that many of the principles of the present invention can be applied to a dual system that employs more than one aerosol generator 66. This may be useful again where high viscosity drug solution is being used, in order to increase the amount of drug that can be delivered. This dual arrangement is also disclosed in the aforementioned U.S. patent application Ser. No. 60/659,919 has been incorporated by reference.

It can thus be appreciated that embodiments of the present invention have now been fully and effectively accomplished. The foregoing embodiments have been provided to illustrate the structural and functional principles of the present invention, and are not intended to be limiting. To the contrary, the present invention is intended to encompass all modifications, alterations and substitutions within the spirit and scope of the appended claims.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A nebulizing device comprising:
a housing, the housing comprising a ventilator interface module and a base module removeably coupled to the ventilator interface module;
an aerosol generator disposed in the base module, the aerosol generator constructed and arranged to nebulize a drug solution provided in the housing;
the ventilator interface module having an outlet port through which nebulized particles of the drug solution can be communicated to a user, and having an inlet port through which the housing receives intake gas;
the housing having a flow path defined therein that directs intake gas from the inlet port to the outlet port such that the nebulized drug solution particles formed in the housing are motivated toward the outlet port when the base module is coupled to the ventilator interface module;
a seal arrangement that substantially seals the inlet port and outlet port from ambient atmosphere when the base module is uncoupled from the ventilator interface module, and such that intake gas can be communicated from the inlet port to the outlet port; and
a separator structure provided in the ventilator interface module that substantially separates larger solution droplets from nebulized drug solution particles formed by the aerosol generator, wherein the separator structure defines a first portion of the flow path from the inlet port to the outlet port when the base module is coupled to the ventilator interface module and wherein the first portion of the flow oath is shaped and positioned to sequentially direct intake gas from the inlet port, through an aerosol region that receives drug solution particles nebulized by the aerosol generator, through the separator structure, and then to the outlet port such that the intake gas carries the nebulized drug solution particles from the aerosol region to the separator structure when the base module is coupled to the ventilator interface module, the aerosol generator is nebulizing drug solution, and intake air is flowing through the inlet port.

2. The device of claim 1, further comprising a second portion of the flow path which bypasses the separator structure when the base module is coupled to the ventilator interface module, and wherein the seal structure seals off the first portion of the flow path from the inlet port and the outlet port when the base module is decoupled from the ventilator interface module.

3. The device of claim 1, wherein the separator structure comprises a return port that returns larger drug solution droplets to a pool of the drug solution contained in the housing.

4. The device of claim 2, wherein the separator structure comprises a separator inlet and a separator outlet, and wherein the seal arrangement comprises engaging surfaces adjacent to the separator inlet and the separator outlet, and wherein the engaging surfaces seal the separator inlet and the separator outlet from the inlet port and the outlet port when the base module is decoupled from the ventilator interface module.

5. The device of claim 4, wherein the separator structure moves to cause the engaging surfaces to seal the separator inlet and separator outlet from the inlet port and the outlet port flow path when the base module is decouple from the ventilator interface module.

6. The device of claim 5, further including a spring that biases the separator structure in a sealing direction, causing the engaging surfaces to seal the separator inlet and separator outlet when the base module is decoupled from the ventilator interface module.

7. The device of claim 6, wherein the separator structure is moved to an unsealing position, against the bias of the spring, when the base module and the ventilator interface module are coupled to one another.

8. The device of claim 1, wherein the flow path directs intake gas directly from the inlet port to the outlet port when the base module is uncoupled from the ventilator interface module.

* * * * *